United States Patent
Rosinger et al.

(10) Patent No.: US 8,673,814 B2
(45) Date of Patent: Mar. 18, 2014

(54) SYNERGISTIC COMBINATIONS WHICH ARE COMPATIBLE WITH CULTIVATED PLANTS AND WHICH COMPRISE HERBICIDES SELECTED FROM THE GROUP CONSISTING OF BENZOYLCYCLOHEXANEDIONES FOR USE IN RICE CROPS

(75) Inventors: Christopher Rosinger, Hofheim (DE); Bernhard Schreiber, Hilden (DE); Lothar Neuwinger, Bad Honnef (DE); Shinichi Shirakura, Oyama (DE)

(73) Assignee: Bayer Cropscience AG, Monheim am Rhien (DE)

( * ) Notice: Subject to any disclaimer, the term of this patent is extended or adjusted under 35 U.S.C. 154(b) by 1276 days.

(21) Appl. No.: 12/141,622

(22) Filed: Jun. 18, 2008

(65) Prior Publication Data
US 2008/0318786 A1  Dec. 25, 2008

(30) Foreign Application Priority Data
Jun. 19, 2007 (DE) .................. 10 2007 028 019

(51) Int. Cl.
*A01N 63/00* (2006.01)
*A01N 43/02* (2006.01)
*A01N 43/00* (2006.01)

(52) U.S. Cl.
USPC ............ 504/118; 504/129; 504/139; 504/140

(58) Field of Classification Search
None
See application file for complete search history.

(56) References Cited

U.S. PATENT DOCUMENTS

| | | | |
|---|---|---|---|
| 5,650,373 A | 7/1997 | Ort et al. | |
| 6,376,429 B1 | 4/2002 | Van Almsick et al. | |
| 6,768,025 B2 * | 7/2004 | Seitz et al. | 568/331 |
| 6,809,064 B2 * | 10/2004 | Auler et al. | 504/134 |
| 6,844,294 B2 * | 1/2005 | Auler et al. | 504/134 |
| 6,884,757 B2 * | 4/2005 | Ziemer et al. | 504/106 |
| 6,919,299 B2 * | 7/2005 | Hacker et al. | 504/141 |
| 2003/0078167 A1 | 4/2003 | Ziemer et al. | |
| 2003/0104940 A1 | 6/2003 | Auler et al. | |
| 2003/0104941 A1 | 6/2003 | Auler et al. | |
| 2003/0158040 A1 | 8/2003 | Hacker et al. | |
| 2007/0010398 A1 | 1/2007 | Rosinger et al. | |

FOREIGN PATENT DOCUMENTS

| | | |
|---|---|---|
| DE | 42 16 880 A1 | 11/1993 |
| EP | 0 274 634 A1 | 7/1988 |
| JP | 55-162703 A | 12/1980 |
| JP | 63-8305 A | 1/1988 |
| JP | 63-201104 A | 8/1988 |
| JP | 63-201105 A | 8/1988 |
| JP | 5-279206 A | 10/1993 |
| JP | 8-268813 A | 10/1996 |
| JP | 2007-320951 | 12/2007 |
| WO | 2004/105482 A2 | 12/2004 |

OTHER PUBLICATIONS

Alanwood, "Compendium of Pesticide Common Names: Herbicides", <http://www.alanwood.net/pesticides/class_herbicides.html>, published Feb. 5, 2007, pp. 1-12.*
International Search Report, PCT/EP2008/004517, Aug. 14, 2009.

* cited by examiner

*Primary Examiner* — Tracy Vivlemore
*Assistant Examiner* — Monica Shin
(74) *Attorney, Agent, or Firm* — Miles & Stockbridge, P.C.

(57) ABSTRACT

Synergistic combinations are provided which are compatible with cultivated plants and which comprise herbicides selected from the group consisting of benzoylcyclohexanediones for use in rice crops
Herbicidal combinations are provided comprising bensulfuron-methyl, benzobicyclon, bromobutide, cyhalofop-butyl, ethoxysulfuron, fenoxaprop-P-ethyl, fentrazamide, pyrazolynate, pyrimisulfan, sulcotrione, tefuryltrione, tembotrione and, if appropriate, isoxadifen-ethyl are described. These combinations exhibit an effect which is superior to that of the herbicides used individually.

16 Claims, No Drawings

US 8,673,814 B2

SYNERGISTIC COMBINATIONS WHICH ARE COMPATIBLE WITH CULTIVATED PLANTS AND WHICH COMPRISE HERBICIDES SELECTED FROM THE GROUP CONSISTING OF BENZOYLCYCLOHEXANEDIONES FOR USE IN RICE CROPS

CROSS REFERENCE TO RELATED APPLICATIONS

This application claims priority from German Application No. 10 2007 028 019.1 filed Jun. 19, 2007, the content of which is incorporated herein by reference.

BACKGROUND OF THE INVENTION

1. Field of the Invention

The invention relates to the technical field of plant protection compositions which can be used against undesirable plant growth and which comprise, as active substances, a combination of at least two herbicides.

2. Description of Related Art

More especially, it relates to herbicidal combinations for use in rice which comprise, as active substances, a herbicide selected from the group consisting of benzoylcyclohexanediones in combination with at least one additional herbicide.

Herbicides from the abovementioned group of benzoylcyclohexanediones are known from numerous documents. Thus, for example, the herbicidal action of numerous such compounds is described in WO 00/21924. Some of the benzoylcyclohexanediones mentioned therein exhibit a satisfactory herbicidal action against harmful plants occurring in rice crops.

However, in practice, there are frequently disadvantages associated with use of the benzoylcyclohexanediones known from these documents. Thus, the herbicidal activity is not always satisfactory or, with a satisfactory herbicidal activity, undesirable damage to the rice plants is observed.

The effectiveness of herbicides depends, inter alia, on the type of herbicide used, the application rate thereof, the composition, the harmful plants to be combated each time, the climatic and soil conditions, and the like. A further criterion is the duration of the action or the rate of degradation of the herbicide. Changes in the sensitivity of harmful plants to an active substance which may occur with relatively long use or in geographically restricted areas are also to be taken into account, if appropriate. Such changes are expressed as a more or less serious loss in activity and can only to a limited extent be compensated for by higher herbicide application rates.

Because of the multitude of possible influencing factors, there is virtually no individual active substance which combines in itself the properties desired for different requirements, in particular with regard to the harmful plant species and the climatic zones. In addition, there is the constant problem of achieving the effect with an ever lower herbicide application rate. A lower application rate reduces not only the amount of an active substance required for the application but generally also reduces the amounts of formulation auxiliaries necessary. Both reduce the economic cost and improve the ecological compatibility of the herbicide treatment.

One method frequently used for improving the application profile of a herbicide consists in combining the active substance of one or more other active substances which contribute the additional properties desired. However, the combined use of several active substances not infrequently results in phenomena of physical and biological incompatibility, e.g. lack of stability of a combined formulation, decomposition of an active substance or antagonism of the active substances. On the other hand, what is desired are combinations of active substances with a favorable activity profile, high stability and the greatest possible synergistically strengthened activity which makes possible a reduction in the application rate in comparison with individual application of the active substances to be combined.

WO 02/089582 and WO 02/085118 describe herbicidal mixtures of particular benzoyl-1,3-cyclohexanediones with various herbicides. WO 02/085120 describes herbicidal mixtures of particular benzoyl-1,3-cyclohexanediones with safeners. However, in practice, there are serious disadvantages to these mixtures. Thus, their compatibility with regard to useful plants, in particular rice, is not always satisfactory and their activity with regard to harmful plants is likewise not always satisfactory.

SUMMARY OF THE INVENTION

It is an object of the present invention to provide herbicidal combinations, in particular for use in rice crops, with improved properties in comparison with the state of the art.

The invention relates to herbicidal combinations, which comprise an effective amount of
A) the compound tembotrione and also the salts thereof normally used in agriculture (component A),
B) a compound selected from the group consisting of benzobicyclon, pyrazolynate, sulcotrione, tefuryltrione and bromobutide (component B), and
C) if appropriate, the safener isoxadifen-ethyl (component C).

The invention likewise relates to herbicidal combinations, which comprise an effective amount of
A) the compound tembotrione and also the salts thereof normally used in agriculture (component A),
B) at least two compounds selected from the group consisting of tefuryltrione, cyhalofop-butyl, fenoxaprop-P-ethyl, fenoxaprop-ethyl, bensulfuron-methyl, ethoxysulfuron, fentrazamide and pyrimisulfan (component B), and
C) if appropriate, the safener isoxadifen-ethyl (component C).

The invention further relates to herbicidal combinations, which comprise an effective amount of
A) the compound tefuryltrione and also the salts thereof normally used in agriculture (component A),
B) at least two compounds selected from the group consisting of cyhalofop-butyl, fenoxaprop-P-ethyl, fenoxaprop-ethyl, bensulfuron-methyl, ethoxysulfuron and fentrazamide (component B), and
C) if appropriate, the safener isoxadifen-ethyl (component C).

DETAILED DESCRIPTION OF THE INVENTION

The combinations according to the invention comprise the components A, B and C in a weight ratio of a:b:c, in which a and b can assume, in each case independently of one another, values of from 1 to 200, preferably 1 to 100, and c can assume a value of from 0 to 200, preferably 0 to 100.

The terms "component A", "herbicide A" and "active substance A" are to be understood as synonymous in the context of the present description. The same applies for the terms "component B", "herbicide B" and "active substance B" and also "component C", "safener C" and "active substance C".

In the combinations according to the invention, it is generally necessary to have application rates in the range from 10 to 1000 g, preferably 10 to 500 g, of active substance per hectare (ai/ha) of the component A and 1 to 1000 g, preferably 5 to 500 g, of the component B. Component C is normally used in an application rate in the range from 0 to 500 g, preferably 0 to 400 g, of active substance per hectare (ai/ha).

Optimum weight ratios can depend on the respective field of application, on the weed spectrum and on the active substance combination used and can be determined in preliminary experiments.

The active substances mentioned above with their common names are well known, for example from "The Pesticide Manual", 14th edition, 2006, British Crop Protection Council, and the website "http://www.alanwood.net/pesticides/". If, in the context of this description, the shortened form of the common name of an active substance is used, this each time includes all common routers, such as the esters and salts, and isomers, in particular optical isomers, in particular the commercially available form or forms. If an ester or salt is described by the common name, this also each time includes all other common derivatives, such as other esters and salts, the free acids and neutral compounds, and isomers, in particular optical isomers, in particular the commercially available form or forms. The chemical compound names given describe at least one of the compounds included under the common name, frequently a preferred compound.

Preference is given to herbicidal combinations comprising the combinations of active substances mentioned below:
tembotrione+benzobicyclon,
tembotrione+pyrazolynate,
tembotrione+sulcotrione,
tembotrione+tefuryltrione,
tembotrione+bromobutide,
tembotrione+benzobicyclon+isoxadifen-ethyl,
tembotrione+pyrazolynate+isoxadifen-ethyl,
tembotrione+sulcotrione+isoxadifen-ethyl,
tembotrione+tefuryltrione+isoxadifen-ethyl,
tembotrione+bromobutide+isoxadifen-ethyl;
tembotrione+tefuryltrione+fentrazamide,
tembotrione+tefuryltrione+cyhalofop-butyl,
tembotrione+tefuryltrione+pyrimisulfan;
tembotrione+tefuryltrione+fentrazamide+isoxadifen-ethyl,
tembotrione+tefuryltrione+cyhalofop-butyl+isoxadifen-ethyl,
tembotrione+tefuryltrione+pyrimisulfan+isoxadifen-ethyl;
tembotrione+bensulfuron-methyl+fentrazamide,
tefuryltrione+bensulfuron-methyl+fentrazamide,
tembotrione+ethoxysulfuron+cyhalofop-butyl,
tembotrione+ethoxysulfuron+fenoxaprop-P-ethyl,
tembotrione+ethoxysulfuron+fenoxaprop-ethyl,
tefuryltrione+ethoxysulfuron+cyhalofop-butyl,
tefuryltrione+ethoxysulfuron+fenoxaprop-P-ethyl,
tefuryltrione+ethoxysulfuron+fenoxaprop-ethyl;
tembotrione+bensulfuron-methyl+fentrazamide+isoxadifen-ethyl,
tefuryltrione+bensulfuron-methyl+fentrazamide+isoxadifen-ethyl,
tembotrione+ethoxysulfuron+cyhalofop-butyl+isoxadifen-ethyl,
tembotrione+ethoxysulfuron+fenoxaprop-P-ethyl+isoxadifen-ethyl,
tembotrione+ethoxysulfuron+fenoxaprop-ethyl+isoxadifen-ethyl,
tefuryltrione+ethoxysulfuron+cyhalofop-butyl+isoxadifen-ethyl,
tefuryltrione+ethoxysulfuron+fenoxaprop-P-ethyl+isoxadifen-ethyl,
tefuryltrione+ethoxysulfuron+fenoxaprop-ethyl+isoxadifen-ethyl.

The combinations according to the invention are very well suited to the selective combating of harmful plants in rice crops.

The combinations according to the invention can be used in all types of application normal for rice herbicides. They are particularly advantageously used in the spray application and in the submerged application. In the submerged application, the paddy water already covers the ground by up to 30 mm at the time of the application. The combinations according to the invention are then directly placed in the paddy water, e.g. in the form of granules. Worldwide, the spray application is used predominantly with seeded rice and the submerged application is used predominantly with transplanted rice.

The combinations according to the invention include a broad weed spectrum. They are suitable for example for the combating of annual and perennial harmful plants, such as, for example, from the species *Abutilon, Alopecurus, Avena, Chenopodium, Cynodon, Cyperus, Digitaria, Echinochloa, Elymus, Galium, Ipomoea, Lamium, Matricaria, Scirpus, Setaria, Sorghum, Veronica, Viola* and *Xanthium*, in particular *Echinochloa* spp., *Leptochloa* spp., *Scirpus* spp., *Cyperus* spp., *Sagittaria* spp., *Monochoria* spp., *Lindernia* spp., *Eleocharis* spp. and *Sesbania* spp.

The herbicidal combinations according to the invention are also distinguished in that the effective dosages of the components A and B used in the combinations are reduced with regard to an individual dosage, so that a reduction in the necessary application rates of the active substances is rendered possible.

The herbicidal combinations according to the invention exhibit, in a preferred embodiment, synergistic effects with simultaneously high compatibility with regard to cultivated plants. The synergistic effects and the high compatibility with regard to cultivated plants can be observed, e.g., with combined application of the components A, B and C; however, it can also frequently be detected when the active substances are applied at different times (splitting). It is also possible to apply the individual herbicides and safeners or the herbicidal safener combinations in several portions (sequential application), e.g. pre-emergence applications, followed by post-emergence applications or early post-emergence applications, followed by medium or late post-emergence applications. Preference is given in this connection to the combined or virtually simultaneous application of the active substances of the herbicide combination according to the invention.

The synergistic effects allow a reduction in the application rates of the individual active substances, a greater potency at the same application rate, the control of species hitherto not included (gaps), an extension of the period of application and/or a reduction in the number of individual applications necessary and, as a result for the user, weed combating systems which are more advantageous economically and ecologically.

The invention also includes those herbicidal combinations which, in addition to the components A, B and C, if appropriate also comprise one or more additional agrochemical active substances with a different structure, such as herbicides, insecticides, fungicides or safeners. The preferred conditions explained above and below are likewise valid for such combinations. These additional agrochemical active substances can be applied both in the combinations according to the invention, as "ready mix", and as "tank mix", by jointly diluting the separately formulated or partially separately formulated components.

The invention likewise also in particular includes those combinations which, in addition to the components A, B and C, also comprise fertilizers, such as ammonium sulfate, ammonium nitrate, urea, potassium nitrate and mixtures thereof. The preferred conditions explained above and below are likewise valid for such combinations.

The invention furthermore also includes those combinations which, in addition to the components A, B and C, also comprise adjuvants, such as emulsifiers, dispersants, mineral and vegetable oils, and mixtures thereof. The preferred conditions explained above and below are likewise valid for such combinations.

The combinations according to the invention can exist both as mixed formulations of the herbicides A and B and also the safener C, if appropriate with additional conventional formulation auxiliaries, which are then used in the conventional way diluted with water, or be prepared as "tank mixes" by jointly diluting the separately formulated or partially separately formulated components with water or with aqueous solutions of fertilizers, for example such as mentioned above.

The combinations according to the invention are very well suited to combating harmful plants, in particular harmful plants in rice crops. Another subject matter of the invention is accordingly a method for combating undesirable plant growth, which comprises applying one or more of the combinations according to the invention to the harmful plants, plant parts thereof or the area under cultivation.

The components A, B and, if appropriate, C can be formulated in different ways, depending on which biological and/or chemical/physical parameters are specified. The following are possible, for example, as general formulation possibilities: wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dustable powders (DP), seed dressings, granules for soil application or broadcasting, water-dispersible granules (WG), ULV formulations, microcapsules or waxes.

The individual formulation types are known in principle and are described, for example, in: Winnacker-Küchler, "Chemische Technologie" [Chemical Technology], Volume 7, C. Hauser Verlag, Munich, 4th edition, 1986; van Valkenburg, "Pesticide Formulations", Marcel Dekker, N.Y., 1973; K. Martens, "Spray Drying Handbook", 3rd Ed., 1979, G. Goodwin Ltd., London. The formulation auxiliaries necessary, such as inert materials, surfactants, solvents and additional additives, are likewise known and are described, for example, in: Watkins, "Handbook of Insecticide Dust Diluents and Carriers", 2nd Ed., Darland Books, Caldwell, N.J.; H. v. Olphen, "Introduction to Clay Colloid Chemistry", 2nd Ed., J. Wiley & Sons, N.Y.; Marsden, "Solvents Guide", 2nd Ed., Interscience, N.Y., 1950; McCutcheon's, "Detergents and Emulsifiers Annual", MC Publ. Corp., Ridgewood, N.J.; Sisley and Wood, "Encyclopedia of Surface Active Agents", Chem. Publ. Co. Inc., N.Y., 1964; Schönfeldt, "Grenzflächenaktive Äthylenoxidaddukte" [Surface-active Ethylene Oxide Adducts], Wiss. Verlagsgesellschaft, Stuttgart, 1976; Winnacker-Küchler, "Chemische Technologie" [Chemical Technology], Volume 7, C. Hauser Verlag Munich, 4th Ed., 1986.

Based on these formulations, combinations with additional pesticidally active substances, such as other herbicides, fungicides or insecticides, and also safeners, fertilizers and/or growth regulators, can also be prepared, e.g. in the form of a ready mix or as tank mix.

Wettable powders are preparations which can be uniformly dispersed in water and which, in addition to the active substance, also comprise ionic or nonionic surfactants (wetting agents, dispersants), e.g. polyoxyethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or sodium oleoylmethyltaurinate, in addition to a diluent or inert substance.

Emulsifiable concentrates are prepared by dissolving the active substance in an organic solvent, e.g. butanol, cyclohexanone, dimethylformamide, xylene or also higher-boiling aromatic compounds or hydrocarbons, with addition of one or more ionic or nonionic surfactants (emulsifiers). Use may be made, as emulsifiers, for example, of: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dustable powders are obtained by milling the active substance with finely divided solid materials, e.g. talc, natural clays, such as kaolin, bentonite and pyrophyllite, or diatomaceous earth.

Granules can be prepared either by spraying the active substance onto adsorptive granulated inert material or by applying active substance concentrates to the surface of carriers, such as sand or kaolinite, or of granulated inert material using binders, e.g. polyvinyl alcohol, sodium polyacrylate or else mineral oils. Suitable active substances can also be granulated in the standard way for the preparation of fertilizer granules, if desired as a mixture with fertilizers. Water-dispersible granules are generally prepared according to methods such as spray drying, fluidized-bed granulation, disk granulation, mixing with high-speed mixers and extrusion without solid inert material.

The agrochemical compositions generally comprise from 0.1 to 99 percent by weight, in particular from 0.2 to 95 percent by weight, of active substances A, B and, if appropriate, C, and also from 99.8 to 5 percent by weight of formulation agents customary in plant protection, the following concentrations being normal according to the type of formulation: in wettable powders, the active substance concentration is, e.g., from approximately 10 to 95 percent by weight, the balance for 100 percent by weight consisting of standard formulation constituents. With emulsifiable concentrates, the active substance concentration can be, e.g., from 5 to 80 percent by weight. Formulations in the form of dust for the most part comprise from 5 to 20 percent by weight of active substance, sprayable solutions from approximately 0.2 to 25 percent by weight of active substance. With granules, such as dispersible granules, the active substance content partly depends on whether the active compound is present in liquid or solid form and on which granulation auxiliaries and fillers are being used. With water-dispersible granules, the content is generally between 10 and 90 percent by weight. In addition, the active substance formulations mentioned comprise, if appropriate, the stickers, wetting agents, dispersing agents, emulsifying agents, preservatives, antifreeze agents, solvents, fillers, colorants, carriers, antifoaming agents, evaporation inhibitors, pH regulators or viscosity regulators which are standard in each case.

For use, the formulations existing in commercially available form are, if appropriate, diluted in the standard way, e.g. using water for wettable powders, emulsifiable concentrates, dispersions and water-dispersible granules. Compositions in the form of dusts, soil granules, granules for broadcasting and sprayable solutions are normally not diluted further with additional inert materials before use.

The active substances can be applied to the plants, plant parts, plant seeds or the area under cultivation (arable land), preferably to the green plants and plant parts and, if appropriate, additionally to the arable land.

One possibility of use is the joint application of the active substances in the form of tank mixes, where the concentrated formulations, which are optimally formulated, of the individual active substances are mixed together in a tank with water and the spray mixture obtained is applied.

A joint herbicidal formulation of the combination according to the invention of components A, B and, if appropriate, C has the advantage of being able to be applied more easily because the amounts of the components have already been adjusted to the correct ratio to one another. Moreover, the auxiliaries in the formulation can be optimally matched to one another, while a tank mix of different formulations can give undesirable combinations of auxiliaries.

A. Formulation Examples a) A dustable powder (DP) is obtained by mixing 10 parts by weight of an active substance/active substance mixture and 90 parts by weight of talc as inert material and comminuting in a hammer mill.

b) A wettable powder readily dispersible in water (WP) is obtained by mixing 25 parts by weight of active substance/active substance mixture, 64 parts by weight of kaolin-comprising quartz as inert material, 10 parts by weight of potassium lignosulfonate and 1 part by weight of sodium oleoylmethyltaurinate as wetting and dispersing agent and milling in a pin mill.

c) A dispersion concentrate readily dispersible in water is obtained by mixing 20 parts by weight of an active substance/active substance mixture with 6 parts by weight of alkylphenol polyglycol ether (Triton X 207), 3 parts by weight of isotridecanol polyglycol ether (8 EO) and 71 parts by weight of paraffinic mineral oil (boiling range, e.g., approximately 255 to 277° C.) and milling in a friction ball mill to a fineness of less than 5 microns.

d) An emulsifiable concentrate (EC) is obtained from 15 parts by weight of an active substance/active substance mixture, 75 parts by weight of cyclohexanone as solvent and 10 parts by weight of oxyethylated nonylphenol as emulsifier.

e) A water-dispersible granule is obtained by mixing
75 parts by weight of an active substance/active substance mixture,
10 parts by weight of calcium lignosulfonate,
5 parts by weight of sodium lauryl sulfate,
3 parts by weight of polyvinyl alcohol and
7 parts by weight of kaolin
milling on a pin mill and granulating the powder in a fluidized bed by spraying on water as granulation liquid.

f) A water-dispersible granule is also obtained by homogenizing and precomminuting
25 parts by weight of an active substance/active substance mixture,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water
on a colloid mill, subsequently milling on a bead mill and atomizing and drying the suspension thus obtained in a spray tower using a single-substance nozzle.

B. Biological Examples

Post-Emergence Weed Action

Seeds or root pieces of harmful mono- and dicotyledonous plants are placed in sandy clay soil in pots, covered with earth and secured in a greenhouse under good growing conditions (temperature, air humidity, water supply). Approximately three weeks after sowing, the plants are treated at the 2- to 3-leaf stage with the herbicidal active substances or the combinations according to the invention. The combinations according to the invention formulated as wettable powders or as emulsion concentrates are sprayed, in spray application, on to the green plant parts in different dosages with a water application rate of 600 to 800 l/ha (corrected). Immediately up to a few days after application, the test receptacles accumulate water over the ground surface by up to 30 mm. With the water application (submerged application), on the other hand, the ground in the closed test receptacle is already covered with the paddy water up to 30 mm at the time of the application. The formulated active substances are here added directly to the paddy water. After an exposure time of the test plants in the greenhouse of an additional 3 to 4 weeks under optimum growing conditions, the effect of the preparations is evaluated visually in comparison with untreated controls. The combinations according to the invention exhibit, even in post-emergence, a very good herbicidal activity against a broad spectrum of economically important harmful plants. In this connection, actions of the combinations according to the invention which exceed the formal sum of the actions of the herbicides when applied individually are frequently observed. The values observed for the tests show, with suitable low dosages, an action of the combinations which lie above the expected values according to Colby.

When the combinations according to the invention are used, herbicidal actions on a harmful plant species which exceed the formal sum of the actions of the herbicides present when applied singly are frequently observed. Alternatively, it can in many cases be observed that a lower application rate for the herbicidal combination is needed in order to achieve, in comparison with the individual preparations, the same action with a harmful plant species. Such improvements in action or improvements in effectiveness or economies in application rate are a strong indication of a synergistic effect.

If the observed activity values already exceed the formal sum of the values for the tests with individual applications, then they likewise exceed the expected value according to Colby, which is calculated according to the following formula and is likewise regarded as an indication of synergy (cf. S. R. Colby in Weeds, 15 (1967), pp. 20 to 22):

$$E = A + B - \frac{A \times B}{100}$$

In this connection:

A, B=action of the component A or B in percent at a dosage of a or b grams ai/ha, E=expected value in % at a dosage of a+b grams ai/ha.

The values observed for the test examples mentioned below are greater than (harmful plants) or lower than (cultivated plants) the expected values according to Colby.

The abbreviations are:

| | | | |
|---|---|---|---|
| BRAPP | *Brachiaria platyphylla* | CYPES | *Cyperus serotinus* |
| ECHCG | *Echinochloa crus galli* | LEFCH | *Leptochloa chinensis* |
| SCPSS | *Scirpus juncoides* | | |
| ORYZA | *Oryza sativa* | | |

TABLE 1

Herbicidal active substances

| Compound | Compound | Compound |
|---|---|---|
| tembotrione: A1 | tefuryltrione: A2 | sulcotrione: B1 |
| ethoxysulfuron: B2 | cyhalofop-butyl: B3 | fenoxaprop-P-ethyl: B4 |
| benzobicyclon: B5 | pyrazolynate: B6 | bromobutide: B7 |
| isoxadifen-ethyl: C1 | | |

TABLE 2

Post-emergence action

| | Dosage | Action/Damage | |
|---|---|---|---|
| Compound | [g a.i./ha] | ORYZA | BRAPL |
| A1 | 12.5 | 10% | 20% |
| B1 | 12.5 | 5% | 0% |
| A1 + B1 | 12.5 + 12.5 | 10% | 60% |
| Colby expected value: | | 24% | 20% |
| Difference: | | −58% | +200% |

TABLE 3

Post-emergence action

| | Dosage | Action/Damage | |
|---|---|---|---|
| Compound | [g a.i./ha] | ORYZA | BRAPL |
| A1 + B2 | 6.25 + 12.5 | 10% | 20% |
| B3 | 6.25 | 0% | 0% |
| A1 + B2 + B3 | 6.25 + 12.5 + 6.25 | 0% | 50% |
| Colby expected value: | | 10% | 20% |
| Difference: | | −100% | +150% |

TABLE 4

Post-emergence action

| | Dosage | Action/Damage | | |
|---|---|---|---|---|
| Compound | [g a.i./ha] | ECHCG | LEFCH | CYPES |
| A1 + B2 + B4 | 12.5 + 25 + 25 | 80% | 40% | 70% |
| C1 | 100 | 0% | 0% | 0% |
| A1 + B2 + B4 + C1 | 12.5 + 25 + 25 + 100 | 100% | 88% | 90% |
| Colby expected value: | | 80% | 40% | 70% |
| Difference: | | +25% | +120% | +29% |

TABLE 5

Post-emergence action

| | Dosage | Action/Damage | |
|---|---|---|---|
| Compound | [g a.i./ha] | ORYZA | BRAPL |
| A2 | 62.5 | 10% | 25% |
| B1 | 12.5 | 5% | 0% |
| A2 + B1 | 62.5 + 12.5 | 10% | 75% |
| Colby expected value: | | 24% | 25% |
| Difference: | | −58% | +200% |

TABLE 6

Post-emergence action

| | Dosage | Action/Damage | |
|---|---|---|---|
| Compound | [g a.i./ha] | ORYZA | LEFCH |
| A2 + B2 | 31.25 + 12.5 | 10% | 55% |
| B3 | 6.25 | 0% | 0% |
| A2 + B2 + B3 | 31.25 + 12.5 + 6.25 | 0% | 75% |
| Colby expected value: | | 10% | 55% |
| Difference: | | −100% | +36% |

TABLE 7

Post-emergence action

| Compound | Dosage [g a.i./ha] | Action against SCPSS |
|---|---|---|
| A1 | 12.5 | 40% |
| A2 | 37.5 | 50% |
| A1 + A2 | 12.5 + 37.5 | 80% |
| Colby expected value: | | 70% |
| Difference: | | +14% |

TABLE 8

Post-emergence action

| Compound | Dosage [g a.i./ha] | Action against SCPSS |
|---|---|---|
| A1 | 12.5 | 40% |
| B5 | 37.5 | 60% |
| A1 + B5 | 12.5 + 37.5 | 90% |
| Colby expected value: | | 76% |
| Difference: | | +18% |

TABLE 9

Post-emergence action

| Compound | Dosage [g a.i./ha] | Action against SCPSS |
|---|---|---|
| A1 | 12.5 | 40% |
| B6 | 250 | 30% |
| A1 + B6 | 12.5 + 250 | 80% |
| Colby expected value: | | 58% |
| Difference: | | +38% |

TABLE 10

Post-emergence action

| Compound | Dosage [g a.i./ha] | Action against SCPSS |
|---|---|---|
| A1 | 12.5 | 40% |
| B7 | 125 | 70% |
| A1 + B7 | 12.5 + 125 | 100% |
| Colby expected value: | | 82% |
| Difference: | | +22% |

TABLE 11

Post-emergence action

| Compound | Dosage [g a.i./ha] | Damage ORYZA |
|---|---|---|
| A1 + A2 + B5 | 25 + 75 + 75 | 80% |
| C1 | 300 | 0% |
| A1 + A2 + B5 + C1 | 25 + 75 + 75 + 300 | 40% |
| Colby expected value: | | 80% |
| Difference: | | −50% |

TABLE 12

Post-emergence action

| Compound | Dosage [g a.i./ha] | Damage ORYZA |
|---|---|---|
| A1 + A2 + B5 | 12.5 + 37.5 + 37.5 | 10% |
| C1 | 300 | 0% |
| A1 + A2 + B5 + C1 | 12.5 + 37.5 + 37.5 + 300 | 0% |
| Colby expected value: | | 10% |
| Difference: | | −100% |

What is claimed is:

1. A herbicidal combination, comprising an effective amount of
   A) tembotrione and/or an agriculturally acceptable salt thereof (component A),
   B) at least two compounds selected from the group consisting of cyhalofop-butyl, fenoxaprop-P-ethyl, and ethoxysulfuron (component B),
   and
   C) if appropriate, the safener isoxadifen-ethyl (component C).

2. A herbicidal combination, comprising an effective amount of
   A) tefuryltrione and an agriculturally acceptable salt thereof (component A),
   B) cyhalofop-butyl and ethoxysulfuron (component B),
   and
   C) if appropriate, the safener isoxadifen-ethyl (component C).

3. A herbicidal combination as claimed in claim 1, wherein the components A, B and C are present in a weight ratio of A:B:C, in which A and B are, in each case independently of one another, values of from 1 to 200 and C is from 0 to 200.

4. A herbicidal combination as claimed in claim 1, wherein the components A, B, and C are present in a weight ratio of A:B:C, in which A and B, are in each case independently of one another, values of from 1 to 100 and C is a value of from 0 to 100.

5. A herbicidal combination as claimed in claim 1, which comprises from 0.2 to 95 percent by weight of active substances A, B and, if appropriate, C, and further comprising from 99.8 to 5 percent by weight of formulation agents customary in plant protection.

6. A herbicide composition according to claim 1, wherein component C is present.

7. A herbicide composition according to claim 2, wherein component C is present.

8. A herbicidal combination, comprising an effective amount of
   A) tembotrione and/or an agriculturally acceptable salt thereof (component A),
   B) pyrazolynate (component B),
   and
   C) if appropriate, the safener isoxadifen-ethyl (component C).

9. A herbicidal combination, comprising an effective amount of
   A) tembotrione and/or an agriculturally acceptable salt thereof (component A),
   B) bromobutide (component B),
   and
   C) if appropriate, the safener isoxadifen-ethyl (component C).

10. A herbicidal combination as claimed in claim 1, wherein the component B is ethoxysulfuron and cyhalofop-butyl.

11. A herbicidal combination as claimed in claim 6, wherein the component B is ethoxysulfuron and fenoxaprop-P-ethyl.

12. A method for combating undesirable plant growth in rice crops, comprising applying at least one herbicidal combination according to claim 1 to a harmful plant, a plant part thereof, or an area under cultivation.

13. A method for combating undesirable plant growth in rice crops, comprising applying at least one herbicidal combination according to claim 2 to a harmful plant, a plant part thereof or an area under cultivation.

14. A method according to claim 12, wherein the component A is applied in an application rate of from 10 to 1000 g of active substance per hectare (ai/ha), the component B is applied in an application rate of from 1 to 1000 g ai/ha and the component C is applied in an application rate of from 0 to 500 g ai/ha.

15. A method according to claim 12, wherein the component A is applied in an application rate of from 10 to 500 g ai/ha, the component B is applied in an application rate of from 5 to 500 g ai/ha and the component C is applied in an application rate of from 0 to 400 g ai/ha.

16. A method according to claim 13, wherein the component A is applied in an application rate of from 10 to 500 g ai/ha, the component B is applied in an application rate of from 5 to 500 g ai/ha and the component C is applied in an application rate of from 0 to 400 g ai/ha.

* * * * *